United States Patent
Elliott et al.

(10) Patent No.: US 8,282,597 A0
(45) Date of Patent: Oct. 9, 2012

(54) SINGLE USE CATHETER

(75) Inventors: Nyle Elliott, Kingwood, TX (US);
Stephen Joel Weiss, Houston, TX (US)

(73) Assignee: Oakington Corp., Kingwood, TX (US)

( * ) Notice: Subject to any disclaimer, the term of this patent is extended or adjusted under 35 U.S.C. 154(b) by 1615 days.

(21) Appl. No.: 10/720,213

(22) Filed: Nov. 25, 2003

(65) Prior Publication Data
US 2005/0113859 A1    May 26, 2005

(51) Int. Cl.
*A61M 29/00* (2006.01)
(52) U.S. Cl. ..................... 604/96.01
(58) Field of Classification Search ............... 604/96.01, 604/97.01, 97.02, 97.03, 98.01, 99.01, 99.02, 604/99.03, 99.04, 284; 606/191–194
See application file for complete search history.

(56) References Cited

U.S. PATENT DOCUMENTS

| | | | |
|---|---|---|---|
| 2,457,244 A | | 12/1948 | Lamson |
| 3,429,314 A | * | 2/1969 | Ericson ............... 604/129 |
| 3,695,921 A | * | 10/1972 | Sheperd et al. ............ 427/2.28 |
| 3,818,903 A | * | 6/1974 | Bleecker .................... 604/98.01 |
| 3,860,007 A | * | 1/1975 | Binard et al. ............ 604/99.02 |
| 4,515,593 A | * | 5/1985 | Norton ........................ 604/265 |
| 4,547,187 A | * | 10/1985 | Kelly ............................ 604/540 |
| 4,751,924 A | * | 6/1988 | Hammerschmidt et al. ................... 128/207.15 |
| 4,813,422 A | * | 3/1989 | Fisher et al. ................. 600/473 |
| 5,234,409 A | * | 8/1993 | Goldberg et al. .......... 604/99.04 |
| 5,293,875 A | * | 3/1994 | Stone ............................ 600/532 |
| 6,682,508 B1 | * | 1/2004 | Meythaler et al. ............ 604/246 |
| 6,723,040 B2 | * | 4/2004 | Brady ............................. 600/29 |
| 6,802,808 B2 | * | 10/2004 | Brady ............................. 600/29 |
| 6,811,559 B2 | * | 11/2004 | Thornton ..................... 606/194 |

FOREIGN PATENT DOCUMENTS

| | | |
|---|---|---|
| EP | 0 282 449 | 9/1988 |
| EP | 0 286 374 | 10/1988 |
| EP | 0 400 369 | 12/1990 |
| JP | 50-28188 | 3/1975 |
| JP | 04-327846 | 11/1992 |
| JP | 10-85247 | 4/1998 |
| JP | 2002-085439 | 3/2002 |
| WO | WO99/43277 | 9/1999 |

* cited by examiner

*Primary Examiner* — Manuel A Mendez
(74) *Attorney, Agent, or Firm* — Welsh Flaxman & Gitler LLC

(57) ABSTRACT

The single use catheter has a lumen with a hydrophobic filter tip at one end. The lumen is divided into two parallel conduits. A first conduit terminates in a one-way valve. A syringe is attached to the one-way valve. Air, saline solution or sterilized water can be introduced through the one-way valve and inflate a cuff about the lumen. The second parallel conduit terminates in a charcoal filter for elimination of bowel gas. The one-way valve prevents deflation of the cuff unless the lumen is cut to allow the fluid from the cuff to exit and deflate the cuff.

4 Claims, 1 Drawing Sheet

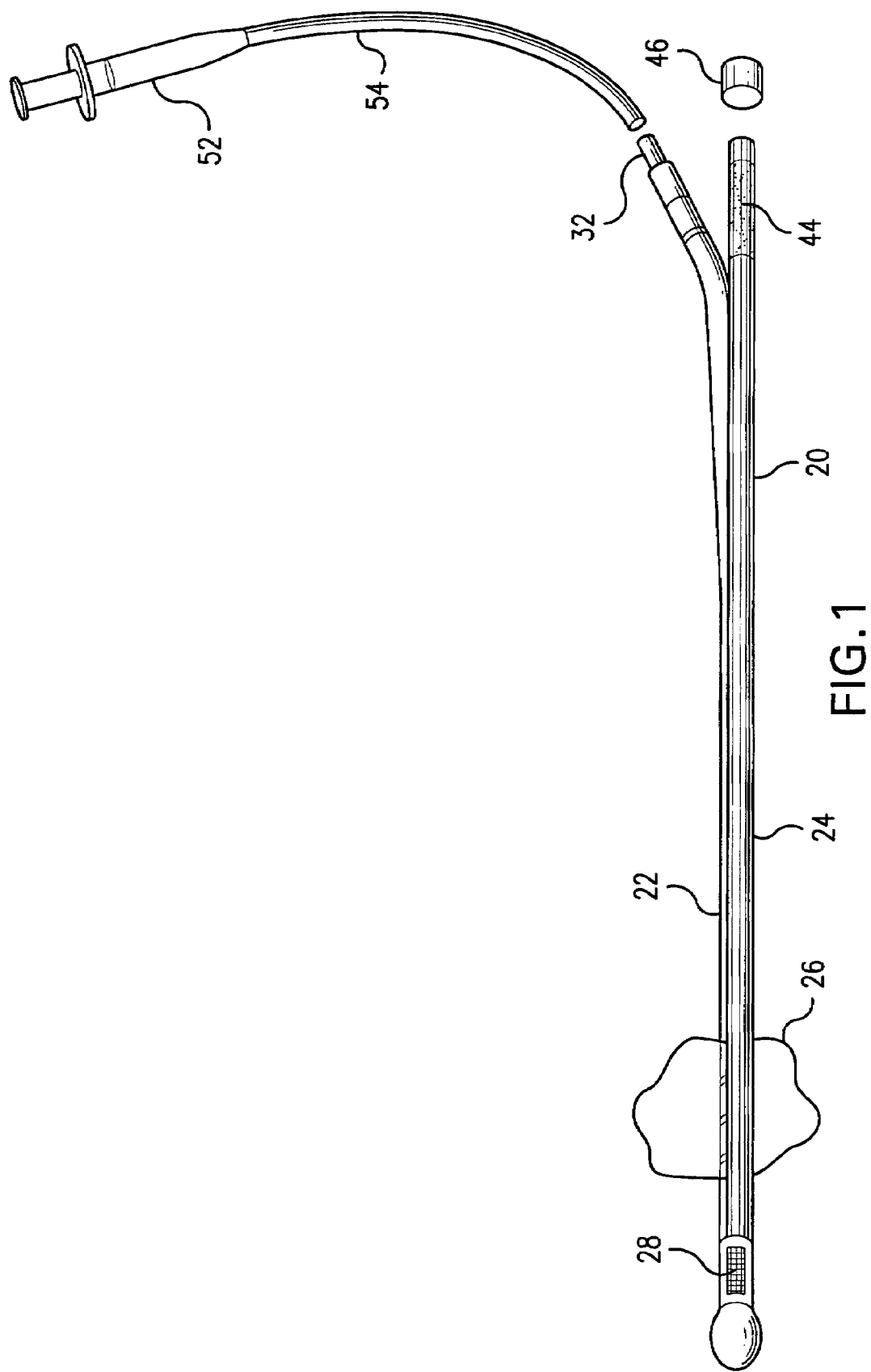

SINGLE USE CATHETER

BACKGROUND OF THE INVENTION

Millions of people suffer with the condition of bowel incontinence. The lack of bowel control causes people embarrassment and unsanitary episodes, quite often leading to social isolation. Treatments for the condition range from conservative treatment to radical treatment such as surgery. However, many patients do not respond to conservative treatment and, for various reasons, are not candidates for surgery.

The prior art discloses devices which are used to help suffer of bowel incontinence with controlling the condition in order to lead a normal lifestyle. One such device is disclosed in U.S. Pat. No. 4,831,422, (Fisher et al). The device is a probe having a dual lumen and inflatable cuff. The transmission and monitoring of reflected IR light generates an alarm signal when a predetermined amount of reflected IR light is measured. IR light is reflected in response to fecal mass.

Most bowel control probes include electronics for sensing and alerting the user to the presence of fecal mass to avoid incontinent episodes. There is a need in the prior art for an inexpensive, single use catheter which can be used to prevent incontinent episodes.

It is an object of the invention to provide an inexpensive bowel catheter.

It is another object of the invention to provide a single use catheter having a one-way valve controlling inflation of a cuff about the catheter.

It is yet another object of the invention to provide a catheter which must be destroyed to allow removal to insure only a single use.

It is another object of the invention to provide a catheter having a hydrophobic filter tip.

These and other objects of the invention will become apparent to ordinary skill in the art after reading the disclosure of the invention.

SUMMARY OF THE INVENTION

The single use catheter has a lumen with a hydrophobic filter tip at one end. The lumen is divided into two parallel conduits. A first conduit terminates in a one-way valve. A syringe is attached to the one-way valve. Air, saline solution or sterilized water can be introduced through the one-way valve and inflate a cuff about the lumen. The second parallel conduit terminates in a charcoal filter for elimination of bowel gas. The one-way valve prevents deflation of the cuff unless the lumen is cut to allow the fluid from the cuff to exit and deflate the cuff.

BRIEF DESCRIPTION OF THE DRAWINGS

FIG. 1 is a side view of the catheter of the invention.

DETAILED DESCRIPTION OF THE INVENTION

Referring to FIG. 1, the single use catheter is formed by a lumen 20 having first 22 and second 24 parallel conduits. The lumen terminates at a distal end in a hydrophobic filter tip 28. Spaced from the filter tip 28 and encircling the lumen 20 is a cuff 26. The cuff 26 is secured in place to the lumen. The first conduit 22 is in fluent communication with the cuff. The conduit 22 extends from the cuff to, and terminates in a one-way valve 32.

A syringe 52 having a tube 54 is connected to the one-way valve 32. The syringe may be a bulb or plunger type. The syringe is charged with 20–25 milliliters of saline or sterilized water. After the tube has been connected to the one-way valve, the syringe is used to inflate the cuff, as will be explained. A second conduit 24 extends from the hydrophobic tip 28 at one end to a filter 44 at the other end. The filter 44 is formed by a charcoal filter sandwiched by two hydrophobic filters. A filter cap is used to close the second conduit 24.

To use the catheter, the user grasps the lumen below the balloon. The lumen is inserted into the annus approximately three inches or a depth recommended by the doctor. Once in place, the syringe is used to inject the sterile water or saline solution through the first conduit 22 to inflate the cuff 26. After inflation, the syringe is disconnected from the one-way valve, as it is no longer needed. Once inflated, the cuff is seated against the sphincter.

The catheter is particularly useful for those patients who are able to maintain a regular schedule of bowel movements. At the appropriate time, as scheduled or as sensed by the user, the catheter can be moved to allow bowel movement. The one-way valve does not allow the discharge of liquid from the cuff in order to deflate the cuff. To deflate the cuff, the user must cut the lumen so that fluid within the cuff is allowed to exit through the first conduit 22. Once deflated, the catheter can be removed.

The tip of the lumen is preferably formed of silicone and contains the hydrophobic filter. The hydrophobic filter presents a barrier to liquids but allows gases to pass through the second conduit 24. The second conduit 24 is provided with charcoal filter 44 to eliminate odors of gases passing through the catheter.

While the invention has been described with reference to a preferred embodiment, variations and modifications would be apparent to one of ordinary skill in the art. The invention is intended to encompass such variations and modifications without departing from the scope of the invention.

We claim:

1. A single use catheter, comprising:
a lumen having a proximate end with a hydrophobic filter tip and a distal end,
an inflatable cuff surrounding said lumen,
said lumen having a first conduit and a second conduit parallel to each other,
said first conduit in fluid communication with said inflatable cuff,
said second conduit in fluid communication with said hydrophobic filter tip at the proximate end of said lumen and where a charcoal filter is located at a distal end of said second conduit,
a port tube at a distal end of said first conduit, and
a one-way valve in said port tube located near said distal end of said first conduit, said one-way valve completely controlling a solution injected into said first conduit and allowing inflation of said inflatable cuff near said proximate end of said lumen, but not allowing deflation whereby said first conduit must be cut to deflate said cuff, wherein said one-way valve controls the entire solution flow into the first conduit for inflation of the cuff.

2. The single use catheter of claim 1, further comprising a syringe attached to said distal end of said port tube.

3. A single use catheter, comprising:
a first conduit having a proximate end with a hydrophobic filter tip and a distal end with a charcoal filter,
a second conduit having a proximate end and a distal end, said second conduit parallel to said first conduit,
an inflatable cuff surrounding said first and second conduits, said first conduit in fluid communication with said inflatable cuff, and a one-way valve in a port tube located at said distal end of said first conduit, said one-way valve completely controlling a solution injected into said first conduit and allowing inflation of said cuff but not allowing deflation whereby said first conduit must be cut to deflate said cuff, wherein said one-way valve controls the entire solution flow into the first conduit for inflation of said cuff.

4. The single use catheter of claim 3, further comprising:
a syringe attached to the distal end said port tube.

* * * * *